(12) United States Patent
Lipkowski

(10) Patent No.: US 8,877,891 B2
(45) Date of Patent: Nov. 4, 2014

(54) METHOD OF PRODUCING A NOVEL OPIOID PEPTIDE

(76) Inventor: Andrej Lipkowski, Warsaw (PL)

( * ) Notice: Subject to any disclaimer, the term of this patent is extended or adjusted under 35 U.S.C. 154(b) by 393 days.

(21) Appl. No.: 13/174,262

(22) Filed: Jun. 30, 2011

(65) Prior Publication Data

US 2012/0004180 A1    Jan. 5, 2012

Related U.S. Application Data

(63) Continuation-in-part of application No. PCT/PL2008/000099, filed on Dec. 31, 2008.

(51) Int. Cl.
*A61K 38/04* (2006.01)
*C07K 5/107* (2006.01)
*A61P 25/04* (2006.01)
*A61K 38/07* (2006.01)
*A61K 38/00* (2006.01)

(52) U.S. Cl.
CPC ............... *C07K 5/1016* (2013.01); *A61K 38/00* (2013.01)
USPC ........ 530/330; 514/21.9; 514/18.4; 514/18.3; 514/1.1

(58) Field of Classification Search
None
See application file for complete search history.

(56) References Cited

U.S. PATENT DOCUMENTS

2006/0241053 A1* 10/2006 Lipkowski et al. .............. 514/16
2010/0273715 A1* 10/2010 Lipkowski et al. ........... 514/18.3
2012/0004180 A1* 1/2012 Lipkowski ................... 514/18.3

FOREIGN PATENT DOCUMENTS

| EP | 2 384 334 B1 | | 2/2013 |
| EP | 2384334 B1 | * | 2/2013 |
| WO | WO 2004014943 | * | 2/2004 |
| WO | WO 2008108673 | * | 9/2008 |

OTHER PUBLICATIONS

Lee et al. Partial retro-inverso, retro, and inverso modifications of hydrazide linked bifunctional peptides for opioid and cholecystokinin (CCK) receptors. Journal of Medicinal Chemistry (2007), 50(1), 165-168 (abstract provided).*
Bonney et al. Spinal antinociceptive effects of AA501, a novel chimeric peptide with opioid receptor agonist and tachykinin receptor antagonist moieties. European Journal of Pharmacology (2004), 488(1-3), 91-99 (abstract provided).*
Maszczynska et al. Alternative forms of interaction of substance P and opioids in nociceptive transmission. Letters in Peptide Science (1998), 5(5-6), 395-398 (abstract provided).*
Iwona Maszczynska Bonney, et al., Spinal Antinociceptive Effects of AA501, A Novel Chimeric Peptide With Opioid Receptor Agonist and Tachykinin Receptor Antagonist Moieties, European Journal of Pharmacology (2004) vol. 488, p. 91-99.
Yeon Sun Lee, et al., Partial-Retro-Inverso, Retro, and Inverso Modifications of Hydrazide Linked Bifunctional Peptides for Opioid and Cholecystokinin (CCK) Receptors, J. Med. Chem. (2007) vol. 50, No. 1, p. 165-168.
Andrzej W. Lipkowski, et al., Biological Activity of Fragments and Analogues of the Potent Dimeric Opioid Peptide, Biphalin, Bioorganic & Medicinal Chemistry Letters (1999) vol. 9 p. 2763-2766.
Iwona Maszczynska, et al., Alternative Forms of Interaction of Substance P and Opioids in Nociceptive Transmission, Letters in Peptide Science (1998) vol. 5, p. 395-398.
International Preliminary Report on Patentability and Written Opinion for International application No. PCT/PL2008/000099.
File History of EP 2 384 334.

* cited by examiner

*Primary Examiner* — Maury Audet
(74) *Attorney, Agent, or Firm* — Vedder Price, P.C.; Thomas Kowalski; Deborah L. Lu

(57) ABSTRACT

The use of opioid peptides of a novel structure is claimed which, in addition to a pharmacophore, additionally contain structural elements reactive with tachykinin receptors. Due to the synergistic reactivity of the opioid with an additional element, an increased analgesic activity is obtained facilitating protracted effective use due to decreased drug tolerance effects. The drugs may particularly be of use in the treatment of chronic pain as effective analgesics during inflammation caused by rheumatism, gout, neurodegenerative states, post-surgical and post-traumatic inflammations or ones induced by tumors.

8 Claims, 1 Drawing Sheet

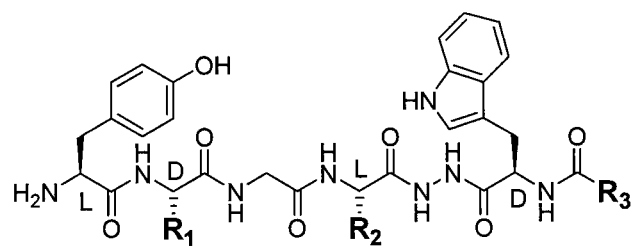

METHOD OF PRODUCING A NOVEL OPIOID PEPTIDE

RELATED APPLICATIONS AND INCORPORATION BY REFERENCE

This application is a continuation-in-part application of international patent application Ser. No. PCT/PL2008/000099 filed 31 Dec. 2008, which published as PCT Publication No. WO 2010/077154 on 8 Jul. 2010.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The subject of the present invention relates to novel peptide analogues exhibiting affinity for opioid receptors, which possess a general formula shown in FIG. 1, especially for administration into the peripheral or central nervous system in the form of a drip, injection or implant for the treatment of strong chronic pain during rheumatoid states or gout or neuropathies connected with osteoporosis, post-surgical or post-accident trauma as well as cancer pain.

BACKGROUND OF THE INVENTION

A pain signal arising from organ damage or disease is transmitted to the central nervous system where it generates the sensation of pain. The magnitude of the pain stimulus is regulated by a system receptors nociceptive and anti-nociceptive located on neuronal cell membranes. Tachykinin receptors located on neurons of the peripheral and central nervous systems constitute a significant component of nociceptive receptors and play a leading role in the transmission of pain signals. Endogenous opioid peptides are a natural factor responsible for mitigating the pain signal as through the activation of anti-nociceptive receptors. Opioid receptors are also activated through the administration of opioid analgesics such as morphine or phentanyl. Unfortunately, the administration of analgesics available to date causes a series of undesirable side-effects, such as tolerance and drug dependency. The use of peptide analogues of natural opioid peptides with the general formula shown in FIG. 1 makes it possible to decrease tolerance and drug dependence. According to results of experiments on animals presented at the International Narcotic Research Conference 1989 and described in post-conference materials, B. S. Silbert, A. W. Lipkowski, D. B. Carr, S. K. Szyfelbein, P. F. Osgood, in the chapter "*Peptides as potential nociceptive drugs.*", pp. 485-488 of "Procc. Int. Narc. Res. Conf.'89", edited by R. Quirion, Alan R. Liss Inc, New York, 1990, as well as D. Kosson, I. Maszczynska Bonney, D. B. Carr, E. Mayzner-Zawadzka, A. W. Lipkowski, in *Antinociceptive properties of biphalin after intrathecal application in rats: a reevaluation.* Pharmacological Report. Vol. 57, pp. 545-549, 2005, an opioid peptide with the common name biphalin exhibits significant analgesic activity. This compound exhibits much lesser habit-forming activity, as described in M. Yamazaki, T. Suzuki, M. Narita, A. W. Lipkowski, "*The opioid peptide analogue biphalin induces less physical dependence than morphine*", Life Science, Vol. 69, pp. 1023-1028, 2001.

Chemically, biphalin is a dimer of two tetrapeptide opioid pharmacophores. Studies on the relationship between biological activity and biphalin structure show that one of the tetrapeptide fragments may be substituted with a peptide or non-peptide lipophilic component without any significant changes in its affinity for opioid receptors, as described in A. W. Lipkowski, A. Misicka, P. Davis, D. Stropova, J. Janders, M. Lachwa, F. Porreca, H. I. Yamamura, V. J. Hruby, in "*Biological activity of fragments and analogues of the potent dimeric opioid peptide, biphalin.*", Bioorganic and Medicinal Chemistry Letters, Vol. 9, pp. 2763-2766, 1999. As a result of substituting one of the tetrapeptide fragments of biphalin with benzoxycarbonyl-L-tryptophan, a compound was produced with affinity for opioid receptors comparable to biphalin, with concurrent activity as a weak tachykinin receptor antagonist. As a result, a compound with strong analgesic properties against inflammatory pain was obtained, as described by I. Maszczynska Bonney, S. E. Foran, J. E. Marchand, A. W. Lipkowski, D. B. Carr in "*Spinal antinociceptive effects of AA501, a novel chimeric peptide with opioid receptor agonist and tachykinin receptor antagonist moieties*", European Journal of Pharmacology, Vol. 488, pp. 91-99, 2004.

Citation or identification of any document in this application is not an admission that such document is available as prior art to the present invention.

SUMMARY OF THE INVENTION

Unexpectedly, it was shown that the alteration of the chirality of the L tryptophan residue to a D-tryptophan residue causes a significant increase in the analgesic activity of the peptide analogue. At the same time, unexpectedly, it was shown that the substitution of the benzoxycarboxyl group with other fragments containing an aromatic group conserves or increases their analgesic activity.

The invention relates to a novel compound with the general formula:

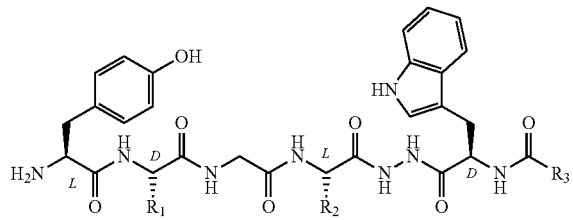

where:
  L, D denote an appropriate amino-acid chirality;
  $R_1$ is an amino-acid residue selected from among: D-alanine, D-Leucine, D-arginine, D-lysine, D-serine or D-threonine,
  $R_2$ is an amino-acid residue selected from among L-phenylalanine or L-tryptophan,
    —CO—$R_3$ denotes benzyloxycarbonyl or cynamoil, alpha-methyl-4-(2-metylopropyl)benzenoacetyl, salicyl-glycyl-, benzoyl-glycyl-,
or its pharmaceutically permissible salt.

Particularly, it may be a compound selected from among:
N'-tyrosyl-D-alanyl-glycyl-phenylalanyl, N"-benzyloxycarbonyl-D-tryptophanyl) hydrazide or its salt, particularly hydrochloride;
N-tyrosyl-D-alanyl-glycyl-phenylalanyl, N'-salicyl-glycyl-D-tryptophanyl) hydrazide or its salt, particularly hydrochloride;
N'-tyrosyl-D-alanyl-glycyl-phenylalanyl, N"-alpha-methyl-4-(2-methylpropyl)benzoacetyl-D-tryptophanyl) hydrazide or its salt, particularly hydrochloride.

The present invention also relates to a method for mitigating, alleviating, reducing or treating pain or inducing an analgesic effect in a mammalian subject which may comprise administering to the subject an analgesic effective amount of a novel compound as disclosed herein. The mammalian subject may be a human or a domestic animal (e.g., dog, cat, horse).

The present invention also relates to an analgesic formulation which may comprise a pharmaceutically or veterinarily acceptable carrier (such as physiological saline) and an analgesic effective amount of a novel compound as disclosed herein.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. §112, first paragraph) or the EPO (Article 83 of the EPC), such that Applicants reserve the right and hereby disclose a disclaimer of any previously described product, process of making the product, or method of using the product.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings.

DETAILED DESCRIPTION OF THE INVENTION

Thus, the first subject of the invention may be a novel compound with the general formula:
FIG. 1 depicts the general formula of compounds being the subject of the patent application, where L, D denote the chiralities of amino-acid residues, R1 denotes residues of D-alanine or D-Leucine or D-arginine or D-lysine or D-serine or D-threonine, R2 denotes a residue of L-phenylalanine or L-tryptophan, and —CO—R3 denotes benzoxycarbonyl or cynamoyl, alpha-methyl-4-(2-methylpropyl)benzacetyl, salicyl-glycyl-, benzoyl-glycyl-.

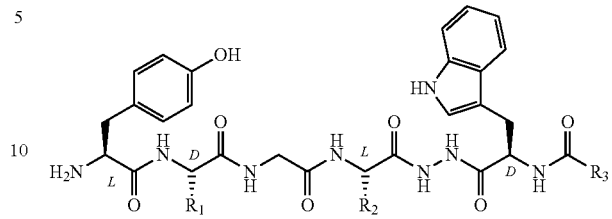

where:
L, D denote an appropriate amino-acid chirality;
$R_1$ is an amino-acid residue selected from among: D-alanine, D-Leucine, D-arginine, D-lysine, D-serine or D-threonine,
$R_2$ is an amino-acid residue selected from among L-phenylalanine or L-tryptophan,
—CO—$R_3$ denotes benzyloxycarbonyl or cynamoil, alpha-methyl-4-(2-metylopropyl)benzenoacetyl, salicyl-glycyl-, benzoyl-glycyl-,
or its pharmaceutically permissible salt.
Particularly, it is a compound selected from among:
N'-tyrosyl-D-alanyl-glycyl-phenylalanyl, N"-benzyloxycarbonyl-D-tryptophanyl) hydrazide or its salt, particularly hydrochloride;
N'-tyrosyl-D-alanyl-glycyl-phenylalanyl, N'-salicyl-glycyl-D-tryptophanyl) hydrazide or its salt, particularly hydrochloride;
N'-tyrosyl-D-alanyl-glycyl-phenylalanyl, N"-alpha-methyl-4-(2-methylpropyl)benzoacetyl-D-tryptophanyl) hydrazide or its salt, particularly hydrochloride.

The next subject of the invention is a use of a compound according to the invention in the production of an analgesic drug.

Novel peptide analogues with the general formula shown in FIG. 1, characterised by a strong affinity for opioid receptors as well as to other receptors involved in the transmission or modulation of pain stimuli, may be of use in the treatment of pain, especially chronic pain caused by disease states, post-operative states or due to accidents.

Drugs containing a compound according to the present invention can be used for peripheral administration or for administration into the central nervous system, preferentially in the treatment of strong chronic pain, particularly those caused by inflammation. In particular, chronic pain and inflammation may be induced by cancer, rheumatoid inflammation, gout, multiple sclerosis, osteoporosis, post-surgical or post-traumatic neuropathies or post-cancer changes. The compounds revealed herein may also demonstrate affinity for tachykinin receptors. It was also observed that the activity of the compound administered peripherally is greatly enhanced during disease states in which inflammation is observed.

A particularly preferential method of administering a compound according to the present invention is an intravenous drip, a subdermal or intraperitoneal implant, and during administration into the central nervous system, a subarachnoid drip or implant. The intravenous drip, a subdermal or intraperitoneal implant or subarachnoid drip or implant may be administered at a dosage of about 1 to 50 mg/kg to mitigate pain and/or eliminate and/or reduce sensitivity to thermal pain. Advantageously, the dosage may be about 1 mg/kg, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg or about 50 mg/kg.

A compound according to the present invention may be administered independently, in the form of a solution, or may be a component of a multi-component array or composition containing other active ingredients.

A compound according to the present invention or its composition with other drugs or carriers may be prepared in the form of a sterile lyophilisate, which should be dissolved prior to administration in a pre-determined volume of physiological saline. Preferentially, a compound or its composition with other drugs and/or carrier substances is prepared in combination with a polymer being a carrier of the active substance.

To better illustrate the nature of the present invention, based on the analgesic activity of compounds shown in FIG. 1, the attached examples demonstrate said activity in animal chronic pain models. The scope of the present invention, however, should not be limited to the contents of the examples below. FIG. 1 depicts the general formula of compounds being the subject of the patent application, where L, D denote the chiralities of amino-acid residues, $R_1$ denotes residues of D-alanine or D-Leucine or D-arginine or D-lysine or D-serine or D-threonine, $R_2$ denotes a residue of L-phenylalanine or L-tryptophan, and —CO—$R_3$ denotes benzoxycarbonyl or cynamoyl, alpha-methyl-4-(2-methylpropyl)benzacetyl, salicyl-glycyl-, benzoyl-glycyl-.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

Example I

T-Butyloxycarbonyl-tyrosyl-D-alanyl-glycyl-phenylalanine (Boc-Tyr-D-Ala-Gly-Phe) (10 mmoles) and benzoxycarbonyl-D-tryptophanyl)-hydrazide (Cbz-D-Trp-NHNH$_2$) (10 mmoles) as well as succinic acid hydroxyimide (HO-Su) (12 mmoles) were dissolved in dimethylformamide (DMF) (40 cm$^3$). Following cooling to 0-5° C., the reaction mixture was supplemented with dicyclohexylcarboxyimide (10 mmoles). The reaction was stirred for 1 hour at a temperature of 5° C., and then for 12 hours at room temperature (20-25° C.). Next, the precipitated dicyclohexylurea (DCU) was filtered out and rinsed twice in 10 cm$^3$ DMF. The filtrate was combined with 100 cm$^3$ of 5% acidic potassium carbonate (KHCO$_3$). The precipitated Boc-Tyr-D-Ala-Gly-Phe-NHNH-(Cbz-D-Trp-) was filtered out and rinsed twice with 10 cm$^3$ of 5% KHCO$_3$, and then twice in 10 cm$^3$ water. The precipitate was dried, and the resulting substance was pulverised and added to 50 cm$^3$ of a concentrated hydrochloric acid and ethanol mixture (1:1). During the reaction, CO$_2$ is released and the reaction product dissolves. After 30 minutes of stirring at room temperature, the ethanol and hydrochloric acid were evaporated off under reduced pressure. The remaining raw product precipitate was recrystallized through dissolution in ethanol and precipitation with ethyl acetate. This resulted in a product, whose elemental analysis as well as mass spectrum correspond to chloral hydrate (N'-tyrosyl-D-alanyl-glycyl-phenylalanyl, N"-benzoxycarbonyl-D-tryptophanyl) hydrazide [HCl.Tyr-D-Ala-Gly-Phe-NHNH-(CBz-D-Trp-)]. 7.5 mmoles of product were obtained.

Inflammation was induced in mice through application of Freund's adjuvant into the limb. A progressing inflammation was observed after two days. After a week, the analgesic effects on acute pain of the peptide analogue HCl.Tyr-D-Ala-Gly-Phe-NHNH-(CBz-D-Trp-) were examined via the immersion of the tail in water at 55° C. Intravenous injection of the peptide analogue at a rate of 20 mg/kg completely mitigated the pain reaction in mice with inflammation.

Example II

T-Butyloxycarbonyl-tyrosyl-D-alanyl-glycyl-phenylalanine (Boc-Tyr-D-Ala-Gly-Phe) (10 mmoles) and salicyl-glycyl-D-tryptophanyl (Salic-Gly-D-Trp-NHNH$_2$) (10 mmoles) as well as succinic acid hydroxyimide (HO-Su) (12 mmoles) were dissolved in dimethylformamide (DMF) (40 cm$^3$). After cooling to 0-5° C., the reaction mixture was supplemented with dicyclohexylcarboxyimide (10 mmoles). The reaction was stirred for 1 hour at a temperature of 5° C., and then for 12 hours at room temperature (20-25° C.). Next, the precipitated dicyclohexylurea (DCU) was drained of and rinsed twice 10 cm$^3$ DMF. The filtrate was mixed with 100 cm3 of 5% acidic potassium carbonate (KHCO$_3$). The precipitated Boc-Tyr-D-Ala-Gly-Phe-NHNH-(Salic-Gly-D-Trp-) was filtered out, rinsed twice in 10 cm$^3$ 5% KHCO$_3$, and then twice 10 cm$^3$ water. The precipitate was dried and pulverised and then added to 50 cm$^3$ of a concentrated hydrochloric acid/ethanol mixture (1:1). During the reaction, CO$_2$ is released and the reaction product dissolves. After 30 minutes of stirring at room temperature, the ethanol and hydrochloric acid were evaporated off under reduced pressure. The remaining raw product precipitate was recrystallized through dissolution in ethanol and precipitation with ethyl acetate. This resulted in a product, whose elemental analysis as well as mass spectrum correspond to chloral hydrate (N'-tyrosyl-D-alanyl-glycyl-phenylalanyl, N'-salicyl-glycyl-D-tryptophanyl) hydrazide [HCl.Tyr-D-Ala-Gly-Phe-NHNH-(Salic-Gly-D-Trp-)]. 7.1 mmoles of product were obtained.

In an animal metastasis model, inflammation was induced by administering around a million cells of murine melanoma into the hind limb. After two days, a progressing inflammation was observed, elicited by tumour take. After two weeks of tumour development, the analgesic activity of (N'-Tyrosyl-D-alanyl-glycyl-phenylalanyl, N"'-salicyl-glycyl-D-tryptophanyl)-hydrazide was examined against acute pain caused by tail immersion in water heated to 55° C. Intraperitoneal injection of the peptide analogue at a rate of 30 mg/kg completely mitigated the pain reaction in mice with inflammation.

Example III t-Butyloxycarbonyl-tyrosyl-D-alanyl-glycyl-phenylalanine (10 mmoles) and alpha-methyl-4-(2-methylpropyl)benzenoacetyl-D-tryptophanyl)-hydrazide (10 mmoles) as well as succinic acid hydroxyimide (HO-Su) (12 mmoles) were dissolved in dimethylformamide (DMF) (40 cm$^3$). After cooling to 0-5° C. dicyclohexylcarboxyimide (10 mmoles) was added to the reaction mixture. The reaction was stirred for 1 hour at a temperature of 5° C., and then for 12 hours at room temperature (20-25° C.). Next, the precipitated dicyclohexylurea (DCU) was drained off and rinsed twice in 10 cm$^3$ DMF. The filtrate was mixed with 100 cm$^3$ of 5% acidic potassium carbonate (KHCO$_3$). The precipitate was filtered out, rinsed twice in 10 cm$^3$ 5% KHCO$_3$, and then twice 10 cm$^3$ water. The precipitate was dried and pulverised and then added to 50 cm$^3$ of a concentrated hydrochloric acid/ethanol mixture (1:1). During the reaction, CO$_2$ is released and the reaction product dissolves. After 30 minutes of stirring at room temperature, the ethanol and hydrochloric acid were evaporated off under reduced pressure. The remaining raw product precipitate was recrystallized through dissolution in ethanol and precipitation with ethyl acetate. This resulted in a product, whose elemental analysis as well as mass spectrum correspond to hydrazide chloral hydrate (N'-tyrosyl-D-alanyl-glycyl-phenylalanyl, N'-salicyl-glycyl-D-tryptophanyl) [HCl.Tyr-D-Ala-Gly-Phe-NHNH-(Salic-Gly-D-Trp-)]. 8.2 mmoles of product were obtained.

Two days prior to the experiments, rats were implanted with cannulae into the subarachnoid cavity. During the experiment, the analgesic activity was examined by administering the peptide analogue (N'-Tyrosyl-D-alanyl-glycyl-phenylalanyl, N''-alpha-methyl-4-(2-methylpropyl)benzenoacetyl-D-tryptophanyl)-hydrazide. A dose of 5 mg of the analogue causes a complete elimination of sensitivity to thermal pain for 1 hours.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A compound having the general formula:

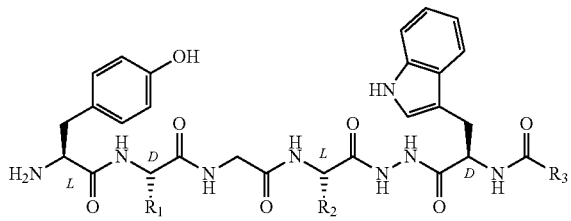

where:
L, D denote an appropriate amino-acid chirality,
$R_1$ is an amino-acid residue selected from among: D-alanine, D-Leucine, D-arginine, D-lysine, D-serine or D-threonine,
$R_2$ is an amino-acid residue selected from among L-phenylalanine or L-tryptophan,
—CO—$R_3$ denotes benzyloxycarbonyl or cynamoil, alpha-methyl-4-(2-metylopropyl)benzenoacetyl, salicyl-glycyl-, benzoyl-glycyl-,
or its pharmaceutically permissible salt.

2. A compound according to claim 1, characterised in that it is a compound selected from among:
N'-tyrosyl-D-alanyl-glycyl-phenylalanyl, N''-benzyloxycarbonyl-D-tryptophanyl hydrazide or its salt;
N'-tyrosyl-D-alanyl-glycyl-phenylalanyl, N'-salicyl-glycyl-D-tryptophanyl hydrazide or its salt; or
N'-tyrosyl-D-alanyl-glycyl-phenylalanyl, N''-alpha-methyl-4-(2-methylpropyl)benzoacetyl-D-tryptophanyl hydrazide or its salt.

3. N'-tyrosyl-D-alanyl-glycyl-phenylalanyl, N''-benzyloxycarbonyl-D-tryptophanyl hydrazide or its salt.

4. N'-tyrosyl-D-alanyl-glycyl-phenylalanyl, N'-salicyl-glycyl-D-tryptophanyl hydrazide or its salt.

5. N'-tyrosyl-D-alanyl-glycyl-phenylalanyl, N''-alpha-methyl-4-(2-methylpropyl)benzoacetyl-D-tryptophanyl hydrazide or its salt.

6. A compound of any one of claims 1, 2, 3, 4 or 5 wherein the salt is a hydrochloride salt.

7. An analgesic comprising a compound of any one of claims 1, 2, 3, 4 or 5.

8. An analgesic comprising a compound of claim 6.

* * * * *